United States Patent
Kumar et al.

(10) Patent No.: US 6,238,697 B1
(45) Date of Patent: May 29, 2001

(54) METHODS AND FORMULATIONS FOR MAKING BUPROPION HYDROCHLORIDE TABLETS USING DIRECT COMPRESSION

(75) Inventors: Vijai Kumar, Morris Plains; Kevin Scott McGuffy, Stanhope, both of NJ (US)

(73) Assignee: Pharmalogix, Inc., Denville, NJ (US)

( * ) Notice: Subject to any disclaimer, the term of this patent is extended or adjusted under 35 U.S.C. 154(b) by 0 days.

(21) Appl. No.: 09/217,641

(22) Filed: Dec. 21, 1998

(51) Int. Cl.[7] .................................. A61K 9/20; A61K 9/26
(52) U.S. Cl. ........................ 424/464; 424/465; 424/469; 424/470
(58) Field of Search ..................................... 424/464, 465, 424/469, 470

(56) References Cited

U.S. PATENT DOCUMENTS

| | | |
|---|---|---|
| 3,671,633 | 6/1972 | Sheth et al. . |
| 4,393,078 | 7/1983 | Peck . |
| 4,404,183 | 9/1983 | Kawata et al. . |
| 4,649,043 | 3/1987 | Urquhart et al. . |
| 4,661,521 | 4/1987 | Salpekar et al. . |
| 4,690,822 | 9/1987 | Uemura et al. . |
| 4,814,263 | 3/1989 | Hine . |
| 4,816,263 | 3/1989 | Ayer et al. . |
| 4,902,514 | 2/1990 | Barclay et al. . |
| 4,925,674 * | 5/1990 | Giannini et al. ..................... 424/469 |
| 5,273,758 | 12/1993 | Royce . |
| 5,358,970 | 10/1994 | Ruff et al. . |
| 5,370,878 | 12/1994 | Shah . |
| 5,427,798 * | 6/1995 | Ludwig et al. ..................... 424/464 |
| 5,453,281 | 9/1995 | Whistler . |
| 5,541,231 | 7/1996 | Ruff et al. . |
| 5,576,024 | 11/1996 | Blase et al. . |
| 5,587,178 | 12/1996 | Slangen . |
| 5,731,000 * | 3/1998 | Ruff et al. ............................ 424/451 |
| 5,733,578 | 3/1998 | Hunter et al. . |
| 5,763,493 | 6/1998 | Ruff et al. . |
| 5,968,553 * | 10/1999 | Maitra et al. ........................ 424/474 |

OTHER PUBLICATIONS

Ansel, et al., (1995) Pharmaceutical dosage forms and drug delivery systems, 6th ed., pp. 199, 213–225.
Handbook of Pharmaceutical Excipients, (1986) American Pharmaceutical Association (APhA). pp. 53–256.
Hercules Klucel (Hydroxypropyl cellulose), Physical and Chemical properties. Bulletin No. 250–2E Rev. 4–97 3M.
Lachman et al. (1996) The Theory and Pracice of Industrial Pharmacy 2nd edition pp. 439–465.
The Merck Index, 12th ed., pp. 246–247.
Remington's Pharmaceutical Sciences (1985). 17th edition, pp. 1603–1632.

* cited by examiner

*Primary Examiner*—Thurman K. Page
*Assistant Examiner*—Todd D Ware
(74) *Attorney, Agent, or Firm*—Jack Matalon

(57) ABSTRACT

Methods and formulations for making extended release bupropion hydrochloride tablets using direct compression, and tablets formed thereby, are provided which combine bupropion hydrochloride, binders such as polyethylene oxide or hydroxypropyl cellulose, a filler such as lactose, glidants and lubricants under low shear conditions to form hard, chip-resistant tablets which exhibit improved cohesiveness and are easily and reproducibly formed without adhering to the compression punches and dies.

23 Claims, No Drawings

METHODS AND FORMULATIONS FOR MAKING BUPROPION HYDROCHLORIDE TABLETS USING DIRECT COMPRESSION

BACKGROUND OF THE INVENTION

Pharmaceutical manufacturers are continuously attempting to improve methods for delivering drugs to enhance and sustain their effects in human therapy. A significant development in drug delivery systems occurred in 1972 with the development of osmotic delivery systems as described by U.S. Pat. Nos. 3,845,770 and 3,916,899. Modifications to the rate-controlling osmotic delivery systems of the prior art are also disclosed in U.S. Pat. Nos. 4,816,263 and 4,902,514.

Such modified osmotic delivery systems use a semipermeable wall to surround an interior containing the drug to be delivered. The external wall is permeable to the passage of an external fluid and may not be permeable to the drug. Such systems may include at least one outlet in the wall for delivering the drug through the osmotic system. The systems operate by absorbing gastric fluid through the semi-permeable wall into the interior of the dosage form at a rate determined by the permeability of the semi-permeable wall and the osmotic pressure gradient across the semipermeable wall. The absorbed fluid produces an aqueous solution containing the drug that is then delivered to the body through at least one opening in the wall.

U.S. Pat. No. 4,816,263 discloses an osmotic device form for delivering isradipine to a biological receptor site in a rate-controlled amount over a prolonged period for cardiovascular therapy. The pharmaceutical dosage form adapted, designed, and shaped as an osmotic drug delivery system is manufactured by wet granulation and includes two compositions which form a bi-layered tablet coated by a semipermeable wall. The first composition includes the drug and contains polyethylene oxide having a molecular weight of 200,000 which is screened through a 40 mesh screen. Specific amounts of isradipine and hydroxypropyl methylcellulose having a molecular weight of 11,200 are added to the polyethylene oxide and slowly mixed with denatured, anhydrous ethanol using a conventional mixer. The wet granulation formed is then passed through a 20 mesh screen, dried at room temperature and passed through the 20 mesh screen again. Magnesium stearate is then added to the granulation and mixed in a roller mill.

The second composition used in the osmotic device is prepared by mixing polyethylene oxide of molecular weight 7,500,000 with sodium chloride in a blender to form a homogeneous blend. The blend is passed through a 40 mesh screen. The mixture is then mixed with a specific amount of hydroxypropyl methylcellulose having a molecular weight of 11,200 and with a specific weight of ferric oxide. Denatured, anhydrous ethanol is slowly added to the blended mixture while mixing again before the wet granulation is screened through a 20 mesh screen. A bi-layered press is used to compress the granulation into two-layered tablets. The tablet is surrounded with a semipermeable wall including 97% cellulose acetate and 3% polyethylene glycol of molecular weight of 3,350. The wall forming composition is dissolved in methylene chloride and methanol to make a 4% solids solution. The wall forming composition is sprayed onto and around the bilaminate in an Aeromatic Air Suspension Coater. The coated tablet is then dried. A 25 mm exit orifice is laser drilled on the laminate side of the osmotic device.

A dosage form for delivering and administering nilvadipine for treating cardiovascular symptoms in a rate-controlled dose over a period of time was developed as described in U.S. Pat. No. 4,902,514. This patent is directed to providing a dosage form manufactured as an osmotic agent that substantially reduces and/or eliminates the unwanted influence of the gastrointestinal environment and still provides controlled administration of nilvadipine over time. The device includes an insoluble coating enclosing the interior within the dosage form. The coating of the dosage form is permeable to the inward passage of exterior fluid present in the gastrointestinal tract into the interior of the dosage form.

In 1987, Urquhart et al. developed an extended-release drug delivery system for delivering a quantity of tiny pills to the gastrointestinal tract. The system includes a pharmaceutical oral capsule prepared with a drug carrier formed of an aqueous polymer and oil capable of controlling the rate of transit of the capsule and the release of the drug from the capsule to the gastrointestinal tract.

Products formulated for controlled-release are generally described as sustained release, prolonged action, depot, repository, delayed-action, retarded-release, and timed-release. Drug products which are formulated for prolonging absorption include dosage forms for oral, injectable and topical use as well as suppositories for insertion in the body cavities. Extended-release tablets are defined herein as pharmaceutical solid dosage forms containing drug substances which are released from the tablet or delivery system over an extended period of time using specific ingredients and includes mechanisms as discussed above such as timed-release, intermittent release and retarded release. They are produced by compression of a formulation containing the drug and certain excipients selected to aid in the processing and release of the drugs. Excipients are classified in accordance with their intended function. Exemplary components for such formulations include fillers, binders, lubricants, and glidants. Without excipients, most drugs and pharmaceutical components cannot be directly compressed into tablets primarily due to the poor flow and/or cohesive properties of most drugs. Extended-release tablets may be coated or uncoated, and are generally formed of powdered, crystalline materials.

Drugs can be administered from a delivery system that releases the drug as it passes through the gastrointestinal tract. Extended-release delivery systems are used because they eliminate the need for multiple dosing. The convenience of extended-release preparations which maintain the blood concentration of the drug at a desired level over a prolonged period of time has been recognized. Extended-release preparations such as a slow-release matrix type tablet in which the ingredients are embedded in a matrix, such as polymeric resins, release the active ingredient by diffusion and erosion.

Most extended-release forms are designed so that the administration of a single dosage unit provides the immediate release of an amount of drug that promptly produces the desired therapeutic effect as well as a gradual and continual release of additional amounts of drug to maintain this level of effect over an extended period of time. In this type of dosage form, the design is based on the particular qualities of each individual drug.

What may be an effective type of dosage form design for one drug may be ineffective in promoting the extended-release of another drug because of peculiar physical, chemical and biological qualities of the different drugs. To maintain a constant level of drug in the system, the drug must be released from the dosage form at a rate that will replace the amount of drug being metabolized and excreted from the body.

Other advantages of extended-release products are reduced side effects and increased patient convenience. These advantages relate to the fact that extended-release preparations maintain the blood concentration of the drug at a desired level over a prolonged period of time which allows patients to reduce the frequency of dosing. This is considered an advantage in ensuring patient compliance in taking medication. Patients required to take one or two dosage units a day are less likely to forget their medication than if they are required to take their medications three or four times a day.

Therefore, there is a need in the art for a drug delivery system that has a sufficiently long transit time in the stomach and acts as an in vivo reservoir, and which releases the drug at a controlled rate and continuously over a prolonged period of time for absorption in the stomach and the intestine.

The method of preparation and type of excipients used in making such dosage forms must be carefully selected to give the formulation the desired physical characteristics that allow for rapid compression of tablets. After compression, the tablets must have a number of additional attributes such as appearance, hardness, and an acceptable dissolution profile. Choice of fillers and other excipients will depend on the chemical and physical properties of the drug, behavior of the mixture during processing, and the properties of the final tablets. Such determinations are typically done by preformulation studies which determine the physical and chemical compatibility of the active component with the proposed excipients. The properties of the drug, its dosage forms and the economics of the process will determine selection of the best process for tableting. Generally, both wet granulation together with direct compression are used in developing a tablet.

The wet granulation method is used to convert a powder mixture into granules having suitable flow and cohesive properties for tableting. The procedure includes mixing the powders in a suitable blender followed by adding a granulating solution under shear to the mixed powders to obtain a granulation. The damp mass is then screened through a suitable screen and dried by tray drying or fluidized bed drying. Alternately, the wet mass may be dried and passed through a mill. The overall process includes: weighing, dry powder blending, wet granulating, drying, milling, blending, lubrication, and compression.

In general, powdered formulations do not have sufficient adhesive or cohesive properties to form strong granules. A binder is usually required to bind the powder particles together due to the poor cohesive properties of most powders. In addition, when processing heat- and moisture-sensitive drugs further precautions must be taken and standard wet granulation methods must be modified to accommodate such drugs. A large number of processing steps are required in tableting moisture- and/or heat-sensitive drugs, and the processes are very time and labor intensive, which increases manufacturing costs. While wet granulation offers the advantage of improving cohesiveness for tableting, it has also been known to reduce the compressibility of some pharmaceutical excipients, such as microcrystalline cellulose.

Direct compression is regarded as a relatively quick process in which the powdered materials are directly compressed without changing the physical and chemical properties of the drug. The active ingredient, direct compression excipients, and other auxiliary substances, such as glidants and lubricants, are blended in a twin-shell or similar blending apparatus before being compressed into tablets. This type of mixing is generally preferred in preparing pharmaceutically acceptable dosage forms. In addition, Remington's Pharmaceutical Sciences (RPS), 17th ed. (1985) states that the manner in which a lubricant is added to a formulation must be carefully controlled. As a result, lubricants may be added to a granulation by gentle mixing. This avoids negative effects on the hardness and disintegration properties of the tablets which can be caused by prolonged blending of a lubricant with a granulation. Similarly, Ansel et al., *Pharmaceutical Dosage Forms And Drug Delivery Systems*, 6th ed. (1995) pp. 199, 213–220 indicates that excessive blending of lubricants with a granulation can cause waterproofing of the granule and reduce the tablet hardness or strength of the compressed tablet. For these reasons, high shear mixing conditions are generally not used to blend lubricants.

Pharmaceutical manufacturers prefer use of direct compression techniques to wet and dry granulation methods because of the lower processing time and the cost advantages. However, direct compression is generally limited to those situations in which the drug or active ingredient has a crystalline structure and physical characteristics required to form pharmaceutically acceptable tablets.

Some active ingredients which do not themselves have the necessary properties for direct compression, can be formed into a directly compressible formulation by incorporating one or more excipients before using direct compression. However, effective excipients for drugs vary with the drug and its properties. As a result, determination of an acceptable combination of excipients which are compatible with each other and with one particular drug, and which are effective for rendering that drug with the excipients compressible would not necessarily operate to render another drug directly compressible into an acceptable dosage form. In addition, each excipient added to the formulation will contribute to increasing the tablet size of the final product. Because tablet size must be within acceptable parameters, there is a limit beyond which increasing tablet size to accommodate additional or increased amounts of excipients to enhance compressibility is not practical. As a result, manufacturers are often limited to using the direct compression method for those formulations which contain a low dose of the active ingredient per compressed tablet such that the formulation may accommodate sufficient excipients to make direct compression practical.

An example of the inability to directly compress a drug can be found with reference to acetaminophen. In U.S. Pat. No. 5,733,578, acetaminophen could not be directly compressed in a formulation including microcrystalline cellulose to form acceptable tablets. The final product tended to be soft, prone to capping, i.e., delamination of one or more of the tablet faces, and was otherwise not pharmaceutically acceptable in that the resulting tablets were so large they would be difficult to swallow. As a result, that patent relied on a time consuming and expensive wet granulation technique for compression of acetaminophen.

U.S. Pat. No. 4,661,521 is also directed to the tableting of acetaminophen, and attempts to use direct compression techniques. However, the acetaminophen could only be directly compressed by including the additional steps of slugging or roller compaction of the tableting mix. In that patent, a fluidized bed apparatus was used for thorough blending of acetaminophen with pregelatinized starch. High shear mixing was used to form a slurry which was fluidized and dried before sizing to achieve the appropriate particle size.

One of the disadvantages of direct compression as a method of tablet manufacturing is the potential size of the compressed tablets. If the amount of active ingredient is high, a pharmaceutical formulator may choose to wet granulate the active ingredient with other excipients to achieve an acceptable tablet size which includes the desired amount of drug. Wet granulation requires less filler, binder, and other excipients than direct compression, because the process of wet granulation contributes toward the desired physical properties, including the compressibility, of the tablet.

Despite the advantages of direct compression, such as reduced processing time and cost, wet granulation is widely used in the industry to prepare solid dosage forms. Wet granulation is often preferred over direct compression, because wet granulation has a greater chance of overcoming any problems associated with the physical characteristics of various ingredients in the formulation. This provides material which has the required flow and cohesive properties necessary to obtain an acceptable dosage form without overloading the tablet formulation with large amounts of excipients.

The popularity of wet granulation over direct compression is based on at least three advantages, in addition to tablet size as discussed above. First, wet granulation provides the material to be compressed with better wetting properties, particularly so in the case of hydrophobic drugs. The addition of hydrophilic excipients makes the surface of the hydrophobic drug more hydrophilic, which reduces disintegration and dissolution problems. Second, the content uniformity of the solid dosage form is generally improved with wet granulation because all of the granules usually contain the same amount of drug. It is important that the particular components of the formulation for a given tablet be consistent to satisfy the necessary quality standards and legal criteria applicable for tablet manufacture, sale and usage. Lastly, the segregation of an active ingredient from excipients is avoided.

Segregation presents a problem in direct compression. The size and shape of particles including the granulate to be compressed are optimized using wet granulation processes. This is because when a dry solid is wet granulated, the binder "glues" particles together and they agglomerate into spherical granules. In direct compression, such granules are not formed and particles of differing size and shape tend to segregate in the blended formulation.

1-(3-chlorophenyl)-2-[(1,1,-dimethylethyl)amino]-1-propanone hydrochloride, referred to herein by its common name of bupropion hydrochloride, an antidepressant, is considered a moderate dose drug. Most tablet formulations include a range of 30–40% by weight of bupropion hydrochloride per tablet. This relatively moderate dose drug, combined with its rather poor physical characteristics for direct compression, has not allowed pharmaceutical manufacturers to use direct compression as a method to prepare the final tablet. Bupropion hydrochloride has poor compressibility and relatively high solubility. The high solubility (about 312 mg/ml (the Merck Index, 12th ed., pp. 246–247)) in aqueous and biological fluids, makes it very difficult to deliver bupropion hydrochloride in any meaningful amounts to biological receptor sites over time. As such, it is essential to control the release rate of bupropion hydrochloride in order to extend its absorption over time. Bupropion hydrochloride is also very hygroscopic and susceptible to decomposition, thereby presenting stability problems. Because of these properties, most manufacturers produce bupropion hydrochloride using the wet granulation method.

In spite of the advantages achieved by wet granulation in tableting bupropion hydrochloride, it would be very advantageous to have a method for the direct compression of tablets having the appropriate dose of bupropion hydrochloride. There is a need in the art for techniques and a formulation including a particular combination of pharmaceutical excipients which would allow for preparation of a specific dose of bupropion hydrochloride tablets by direct compression to avoid the time and expense involved with manufacturing using wet granulation techniques.

In addition to a need for an improved, more economical tableting process for bupropion hydrochloride, a dosage form is needed which provides for improved extended-release delivery of the drug. Due to the relatively high solubility of bupropion hydrochloride in aqueous and biological fluids as well as its susceptibility to decomposition, it is imperative that the release be controlled in order to increase the drug's therapeutic effectiveness. As such, in developing a more economical process for bupropion hydrochloride, care must be taken to ensure that the release profile is at least comparable to, if not better than, release rates achieved by tablets which are formed in accordance with existing wet granulation tableting methods.

SUMMARY OF THE INVENTION

The invention includes a method for making bupropion hydrochloride tablets which comprises weighing bupropion hydrochloride and excipients, combining the bupropion hydrochloride and the excipients to form a directly compressible formulation, and compressing the formulation to form bupropion hydrochloride tablets.

In one embodiment, the method further comprises weighing the excipients such that the directly compressible formulation comprises on a solids basis from about 30 to about 40 percent by weight of bupropion hydrochloride, from about 10 to about 20 percent by weight of a binder, from about 40 to about 60 percent by weight of a filler, from about 0.1 to about 2 percent by weight of a glidant, and from about 0.1 to about 2 percent by weight of a lubricant.

The invention further includes a directly compressible bupropion hydrochloride formulation which comprises bupropion hydrochloride, a binder, a glidant and a lubricant.

The invention also includes a bupropion hydrochloride tablet formed by direct compression of a formulation comprising, on a solids basis, from about 30 to about 40 percent by weight bupropion hydrochloride, from about 10 to about 20 percent by weight of a binder, from about 0.1 to about 2 percent by weight of a glidant, from about 0.1 to about 2 percent by weight of a lubricant, and from about 40 to about 60 percent by weight of a filler.

In a further embodiment, the invention includes a method for making bupropion hydrochloride tablets having from about 100 mg to about 150 mg of bupropion hydrochloride by direct compression. The method comprises combining the bupropion hydrochloride, a binder, and a filler to form a mixture. A lubricant and a glidant are then combined with the mixture to form a directly compressible formulation. The formulation is directly compressed to form the bupropion hydrochloride tablets. The formulation comprises, on a solids basis, from about 30 to about 40 percent by weight of bupropion hydrochloride, from about 10 to about 20 percent by weight of binder, from about 0.1 to about 2 percent by weight of glidant, from about 0.1 to about 2 percent by weight lubricant, and from about 40 to about 60 percent by weight filler.

DETAILED DESCRIPTION OF THE INVENTION

The present invention is directed to direct compression methods for forming bupropion hydrochloride, direct compression formulations for bupropion hydrochloride and tablets formed from the methods and formulations. The present invention provides a significant advancement in the art in that it provides methods and formulations which allow for an efficient and economical method of preparing bupropion hydrochloride without using complicated techniques such as wet granulation, slugging, roller compaction or chilsonation. The method and formulations of the present invention may be used for forming extended-release tablets of bupropion hydrochloride which provide extended release profiles comparable to those of bupropion hydrochloride tablets formed using wet granulation processes, and show an acceptable in vitro dissolution profile.

The formulations of the present invention include excipients which still allow for accommodation of the pharmaceutically preferred moderate dosage of bupropion hydrochloride for treatment. In the preferred embodiment, the formulation also provides the advantages of slow release of the active ingredient over an extended period of time.

The extended release mechanism of the present invention is derived from a semipermeable wall surrounding the interior which includes the bupropion hydrochloride formulation. The wall has relatively high solubility in aqueous and biological fluids and an expandable hydrogel. Bupropion hydrochloride is released slowly through the diffusion and erosion matrix containing polyethylene oxide or hydroxypropyl cellulose. The extended release formulation for forming tablets includes a reservoir of the formulation which provides an expandable material.

The formulations of the present invention also have a high level of solubility and extended-release activity by compressing bupropion hydrochloride along with the preferred excipients as described below.

The invention provides a method for preparing a sustained action, or extended-release solid dosage form of bupropion hydrochloride, preferably in a moderate dose dosage form, using direct compression.

The method includes weighing the bupropion hydrochloride and excipients and combining the bupropion hydrochloride and excipients to form a directly compressible formulation. The formulation is then compressed to form bupropion hydrochloride tablets. In the directly compressible formulation, the excipients include, but are not limited to, lubricants, diluents and binders, glidants and fillers. The excipients provide good flow and compression characteristics to the bupropion hydrochloride for direct compression.

In the formulation of the invention, the binders also function as diluents in that they not only act to impart cohesive qualities to the material within the formulation, but also tend to increase the bulk weight of the directly compressible formulation to achieve an acceptable formulation weight for direct compression. Applicants have discovered that by using the particular excipients described herein, the hygroscopic, sensitive and incompressible nature of the bupropion hydrochloride is overcome allowing for a formulation exhibiting good cohesion and directly compressible properties.

The formulation includes excipients which preferably have particle sizes within given preferred ranges as set forth below to allow for improved homogeneity of the powder mix and to minimize segregation. In addition the excipients were selected to achieve good content uniformity and to ensure the slow release of the active ingredient. The excipients, by having excellent binding properties, and homogeneity, as well as good compressibility, cohesiveness and flowability in blended form, minimize segregation of powders in the hopper during direct compression.

In preparing the formulation, and weighing the bupropion hydrochloride as the active ingredient, it is preferred that this component be provided as 1-(3-chlorophenyl)-2-[1,1-dimethylethyl)amino]-1-propanone hydrochloride in a form which may be from about 98 to about 100% pure. It is further preferred that the active ingredient be provided as a white crystalline powder of a particle size which ranges from about 130 to about 450 microns, typically being capable of passing through a mesh size accommodating approximately 132–446 microns. All particle size ranges referred to herein represent an average particle size and are measured in accordance with standard methods known to those of ordinary skill in the art. More preferably, the bupropion hydrochloride powder has a particle size distribution in which 50% of the particles are less than or equal to about 197 microns and 90% of the particles are less than or equal to about 424 microns.

The density of the powdered bupropion hydrochloride is preferably from about 0.44 to about 0.66 g/ml. It will be understood, based on this disclosure, that the density and vicosity information and ranges provided herein for the bupropion hydrochloride and various excipients are the preferred embodiment, and that the invention is not limited by the preferred embodiments. The commercially available forms of bupropion hydrochloride for use in making tableting formulations and in the present invention are freely soluble in water and are, without providing the preferred excipients as set forth herein, inherently non-compressible in nature. Standard precautions in handling the bupropion hydrochloride powder due to its hygroscopic nature are preferably observed to minimize moisture exposure during storage and transit. In addition, excipients such as those described below, may be included with the bupropion hydrochloride.

The bupropion hydrochloride is preferably weighed and combined in the formulation such that the resulting tablet includes a dosage of from about 100 to about 150 mg per tablet. In the preferred formulation, bupropion hydrochloride, in order to achieve this dosage level, will be weighed to make up from about 30 to about 40 weight percent of the directly compressible formulation. However, it should be understood, based on this disclosure, that the amount of bupropion hydrochloride provided depends on the desired dosage amount per tablet. The amount of bupropion hydrochloride and of the excipients can be varied accordingly provided suitable direct compressibility properties are achieved.

The excipients preferably include a binder, a filler, a glidant and a lubricant. The binder may also function as a diluent as set forth above, and the formulation may include other excipients in the formulation provided the compressibility properties are not significantly affected. The binder should be present in the formulation in an amount of from about 10 to about 20 percent by weight on a solids basis in comparison with the total weight of the formulation. While the binder can be varied, it is preferred that the binder include either polyethylene oxide or hydroxypropyl cellulose. If using polyethylene oxide, it is preferred that the polyethylene oxide be present in an amount of from about 10 to about 20 percent by weight of the formulation on a solids basis. While polyethylene oxide is known for use as a binder material for other formulations, it has not been used for the direct compression formulations for bupropion hydrochloride, particularly since bupropion hydrochloride is generally viewed as unsuitable for direct compression processing. Suitable polyethylene oxides are described in U.S. Pat. No. 5,273,758 which is incorporated herein by reference in its entirety.

Preferably, however, the polyethylene oxide has a molecular weight ranging form about 300,000 to about 5,000,000, more preferably from about 600,000 to about 5,000,000, and most preferably about 5,000,000, i.e., a high molecular weight polyethylene oxide. It is further preferred that the average particle size ranges from about 840 to about 2,000 microns. The density of the polyethylene oxide preferably ranges from about 1.15 to about 1.26 g/ml and the viscosity from about 8,800 to about 17,600 cp. The polyethylene oxide functions as a binder and diluent in the directly compressible formulation.

The polyethylene oxide used in the directly compressible formulation is preferably a homopolymer having repeating oxyethylene groups, i.e., —(—O—CH$_2$—CH$_2$—)$_n$—, where n can range from about 2,000 to about 180,000. Preferably, the polyethylene oxide is a commercially available and pharmaceutically acceptable homopolymer having a moisture content of no greater than about 1% by weight. Examples of suitable, commercially available polyethylene oxide polymers include Polyox® WSRN-1105 and/or WSR-coagulant, available from Union Carbide. The preferred polyethylene oxide powdered polymers contribute to a consistent particle size within the combined directly compressible formulation and eliminate the problems of lack of content uniformity and possible segregation. The high viscosity and density play a role in slowing the release of bupropion hydrochloride from the tablets.

The granular polyethylene oxide also contributes to the effective dissolution of the bupropion hydrochloride tablets. The polymer is a water soluble resin which forms a dynamic hydrophilic matrix system to allow for slow release of bupropion hydrochloride in a patient's body. Upon exposure to water, the polyethylene oxide will hydrate and swell rapidly to form a hydrogel whose properties are excellent for controlled drug delivery. As a result, by achieving homogeneity of excipients and bupropion hydrochloride, and incorporating polyethylene oxide, the polyethylene oxide provides for a hydrophilic matrix tablet. The drug release mechanism is controlled by variables such as surface area and diffusion rate in a dynamic process.

When the tablet is wet, the polymer on the tablet surface hydrates and forms a gel layer. The bupropion hydrochloride diffuses from the surface of the gel layer, which expands with time into the interior of the tablet, allowing for diffusion of the bupropion hydrochloride from the tablet core. Polyethylene oxide is selected in accordance with the preferred parameters noted above to provide very hydrophilic properties combined with rapid hydration to form a gel layer on the tablet surface for slow release of the drug. The preferred grade of polyethylene oxide preferably used is non-ionic, to minimize interaction between the drug and the polymer such that there is substantially no interaction. The dissolution rate of bupropion hydrochloride is dependent on the rate of drug diffusion out of the wet gel and the rate of tablet erosion.

The hydration rate is related to the number of repeating oxyethylene units in the polymer. The higher the number of repeating units, the faster the hydration of the polymers due to the hydrophilic nature of the repeating units, the faster the infusion and gel migration into the tablet and the faster the release of the drug. The polymer grade contributes to determining the rate of hydration. Preferably, from about 10 to about 20 percent by weight polyethylene oxide is provided to the directly compressible formulation on a solids basis, and the polymer is weighed accordingly to achieve a dosage form having from about 100 to about 150 mg bupropion hydrochloride per tablet. The amount may be more or less depending on the amount of other excipients present. The amount of polyethylene oxide can also be varied depending on the dosage size and desired rate of release.

The binder in the directly compressible formulation alternatively may include a pharmaceutically acceptable hydroxypropyl cellulose which may function as a binder and a diluent. Hydroxypropyl cellulose as a binder would also function to assist and/or control the rate of dissolution of the resulting tablet. Hydroxypropyl cellulose in polymeric form creates a dynamic hydrophilic matrix system that slows the release of the bupropion hydrochloride. The hydroxypropyl cellulose hydrates partially by wetting following tablet ingestion and forms a gel layer. An initial burst of bupropion hydrochloride is released following initial hydration. Water then permeates into the tablet and adds to the increasing thickness of the gel layer while the bupropion hydrochloride diffuses out of the gel layer. The bupropion hydrochloride extended-release tablet eventually is fully hydrated and gradually releases into the aqueous medium. Water continues to move towards the tablet core during the process while bupropion hydrochloride is released by diffusion from the gel layer and by exposure caused by tablet erosion. The high solubility of the other excipients aids in hydrating the outer layer of the tablet to form a gel layer. The dissolution rate of bupropion hydrochloride depends on the rate of drug diffusion out of the wet gel and the rate of tablet erosion.

It is preferred that if hydroxypropyl cellulose is used in the formulation, it is in particle form with a preferred average particle size of from about 175 to about 600 microns, typically to pass through a mesh of 177–590 microns, although the size may vary depending on the size of the other excipients. The density preferably ranges from about 0.3 to about 0.7 g/ml and the viscosity from about 300 to about 3,000 cp. The hydroxypropyl cellulose should have a molecular weight of preferably from about 70,000 to about 1,150,000. Selecting a hydroxypropyl cellulose having these characteristics functions within the formulation to provide homogeneity within the final directly compressible formulation and helps minimize problems associated with a lack of content uniformity and segregation. The high viscosity and density contribute to slowing the rate of release of bupropion hydrochloride from the tablets. Hydroxypropyl cellulose effectiveness is optimal when it is present in an amount of from about 10 to about 20 percent by weight on a solids basis of the formulation.

The formulation may also comprise other known fillers which impart cohesive qualities to the powdered material in combination with the preferred binders provided that the compressibility properties of the formulation are not significantly affected, for example, sodium starch glycolate, corn starch, talc, sucrose, dextrose, glucose, lactose, xylitol, fructose, sorbitol, calcium phosphate, calcium sulfate, calcium carbonate, and mixtures thereof. Microcrystalline cellulose may also be used as a filler and may be any suitable form of microcrystalline cellulose as is known and used in the tableting art.

Preferably, lactose is used as a general filler in the formulation, and is preferably provided in greater amounts than such other additive fillers. While such additional fillers as noted above may be included for cost savings purposes or to achieve modified properties, their presence should be minimized and any such additional fillers be selected to have particle size, density, and viscosity characteristics which would not significantly affect the homogeneity or compressibility of the formulation or the dissolution profile of the formed tablets.

Any additional fillers need not provide the same level of cohesive properties as the binders selected, but are preferably otherwise capable of contributing to formulation homogeneity and resist segregation from the formulation once blended Further, such fillers should not have a detrimental effect on the flowability of the composition or dissolution profile of the formed tablets. It is preferred that any such fillers be selected with flow properties and particle size profiles compatible with those of the other excipients as described herein.

Preferably, a pharmaceutically acceptable lactose in anhydrous form which demonstrates an increase in compressibility, has good binding characteristics and provides sufficient hardness to tablets formed in accordance with the invention is provided as the preferred filler in the formulations of the invention. The use of lactose as a preferred filler enables the formulation used in the method of the invention to form hard, strong tablets at low machine pressure which reduces instances of chipping and capping of the tablets as well as reducing the friability of the tablets. The grade of lactose chosen has been determined in the course of the evaluation of the formulations of the invention to contribute to improved, superior flow properties as well as to enhancing lubrication of the powders in the die cavity and on punch faces for forming indentations on the tablet surface such that the lactose aids in preventing adherence of tablets to the punches during compression. Lactose contributes to many favorable properties in the tablet and functions well within the overall formulation.

Preferably, filler(s) are present in an amount of from about 40 to about 60 percent, and more preferably from about 45 to about 55 percent by weight on a solids basis of the directly compressible formulation. Most preferably, the only filler is lactose, anhydrous, in an amount as noted above and having a density of from about 0.5 to about 1.0 g/ml, with a preferred bulk density of about 0.678 g/ml. In addition, preferably the lactose has a particle size distribution in which from 25–50% of the lactose particles have a particle size of less than or equal to 106 microns, and from 55–75% of the particles have a particle size of less than or equal to 75 microns.

The formulation for the method of the invention also preferably includes at least one glidant and at least one lubricant. The glidants and lubricants may be any suitable glidants and lubricants which contribute to the compressibility, flowability and homogeneity of the formulation and which minimize segregation and do not significantly interfere with the slow release mechanism of the binders as set forth above. Preferably, the glidant is selected to improve the flow of the formulation and includes colloidal silicon dioxide. It is preferred that colloidal silicon dioxide having a density of from about 0.029 to about 0.040 g/ml be used to improve the flow characteristics of the formulation and be provided in an amount of from about 0.1 to about 2 percent by weight of the formulation on a solids basis. The preferred colloidal silicon dioxide has a BET surface area of 175 to 225 $m^2$/g, a density of from about 35 to about 40 g/l and a nominal particle diameter of 14 nm. It will be understood, based on this disclosure, however, that while colloidal silicon dioxide is preferred as a glidant, other glidants having similar properties which are known or to be developed could be used provided they are compatible with the other excipients and the bupropion hydrochloride in the formulation and which do not significantly affect the flowability, homogeneity and compressibility of the formulation.

The lubricant may be any lubricant which substantially prevents segregation of the powder by contributing to homogeneity of the formulation and which exhibits good flowability. Preferably the lubricant functions to facilitate compression of the tablets and ejection of the tablets from the die cavity. Such lubricants may be hydrophilic or hydrophobic and can include magnesium stearate, Lubritab®, stearic acid, talc and other lubricants known in the art or to be developed which exhibit acceptable or comparable properties.

Preferably the lubricant is magnesium stearate which exhibits excellent properties in combination with the other preferred excipients of the formulation. Magnesium stearate contributes to reducing friction between the die wall and tablet formulation during compression and to the easy ejection of the bupropion hydrochloride tablets. It also resists adhesion to punches and dies. The lubricant, such as magnesium stearate, should be selected to aid in the flow of the powder in the hopper and into the die. Most preferably, magnesium stearate having a particle size of from about 5 to about 50 microns and a density of from about 0.1 to about 1.1 g/ml is used in the formulation. Lubricant should make up from about 0.1 to about 2 percent by weight of the formulation on a solids basis. Such lubricant is stable and does not polymerize within the formulation once combined. However, in one preferred embodiment of the invention, the other excipients and the bupropion hydrochloride are combined first and the lubricant is added to the other excipients and the bupropion hydrochloride after they have been initially thoroughly combined.

Other components, such as flavors, colors, inserts and the like which are standard in the art or to be developed may also be provided so long as they do not significantly affect the flowability, homogeneity, direct compressibility of the tablet formulation or dissolution profile of the finished tablets. Preferably such components collectively represent no greater than about 10 percent by weight, and more preferably are no greater than 2 percent by weight of the formulation on a solids basis.

Stabilizers or preservatives for bupropion hydrochloride or for the other excipients in the formulation which may be moisture-sensitive, including stabilizers such as organic acids, carboxylic acids, acid salts of amino acids, and sulfites such as potassium metabisulfite and sodium bisulfite may also be included in the formulation or be provided within the bupropion hydrochloride used to prepare the formulations of the present invention. Such stabilizers are preferably present in amounts of less than about 20 weight percent, more preferably less than about 10 weight percent, and most preferably, less than about 5 weight percent of the entire formulation on a solids basis. Suitable stabilizers are also described in U.S. Pat. No. 5,541,231, herein incorporated by reference.

The method of the invention does not require granulation, slugging or roller compaction, and the formulation can be directly compressed into tablet form using any suitable compression apparatus useful for forming pharmaceutical grade tablets. Preferably, the tablets are compressed using any suitable rotary tablet press such as a Stokes, Manesty, and the like. The tablets formed preferably are compressed to achieve a hardness of from about 5 to about 12 kp and a thickness, for the preferred formulation, of from about 0.170 in (0.431 cm) to about 0.195 in (0.495 cm), although these amounts may be varied for different affects or manufacturing specifications. The tablet thickness is measured in a direction perpendicular to the longitudinal plane of the tablet and represents the largest measurement made in that direction, i.e., the maximum thickness.

The preferred formulation, as described above, may be combined by blending, mixing, stirring, shaking, tumbling, rolling or by any other method of combining powdered components to achieve a homogeneous blend. However, it is most preferred that the excipients and the active ingredient, bupropion hydrochloride are combined using a V-blender, twin shell blender or similar apparatus capable of functioning under preferred low shear conditions. Impellers, knives, or other rotating blades may be used to facilitate combining the formulation ingredients. However, it is preferred that such mixing attachments be used within acceptable low shear parameters. While high shear conditions can be used when combining the formulation components, low shear conditions are preferred to achieve a thorough, homogeneous blend of the powdered components with little and substantially no segregation and without having a significant effect on the selected particle sizes of the various components as noted above. It is also preferred, in one embodiment of the method of the invention, that the lubricant and glidant be added last after thorough blending of the other components of the formulation.

Acceptable low shear conditions useful in the method of the invention should include a mixing speed for any agitation apparatus such as an impeller of from about 4 to about 30 rpm, and more preferably from about 25 to about 30 rpm. Alternatively, the formulation may be tumbled or rotated for blending at a speed of from about 250 to about 350 ft/min. The invention should not be considered limited to these particular conditions for combining the components and it will be understood, based on this disclosure that the advantageous properties can be achieved through other conditions provided the components retain their basic properties and substantial homogeneity of the blended powdered components of the formulation is otherwise achieved without any significant segregation.

In addition to the method described above, the invention includes a directly compressible bupropion hydrochloride formulation which includes bupropion hydrochloride, a binder which preferably includes polyethylene oxide or hydroxypropyl cellulose, a glidant and a lubricant. The formulation is preferably an extended release formulation which provides a slow release delivery of bupropion hydrochloride. The preferred dosages include 100 or 150 mg, but may be varied for different effects and patient treatments as noted above.

The binder, glidant and lubricant may be any acceptable binders, glidants and lubricants as described above. Preferably the formulation includes one or more of the fillers described above as well. Preferred formulation ranges are as described above and are summarized in Table A below. However, the formulation should not be considered limited to the ranges shown and may be adjusted in accordance with the disclosure for various formulations provided flowability, powder homogeneity and compressibility are maintained and provided the dissolution profile is not significantly affected.

TABLE A

| Component | Weight Percentage Range (%) |
| --- | --- |
| Bupropion hydrochloride | 30–40 |
| Binder | 10–20 |
| Glidant | 0.1–2 |
| Lubricant | 0.1–2 |
| Filler | 40–60 |

Also within the scope of the invention are bupropion hydrochloride tablets formed from direct compression of a formulation including the components in the amounts for the formulation used in the method as described above. Preferably, the tablets have the above-noted preferred degrees of hardness, and preferred maximum thickness and dosage criteria.

The invention will now be described with reference to the following non-limiting examples. In each of the examples, commercial components used in forming the various preferred formulations are as set forth below:

EXAMPLE 1

A direct compression formulation for an extended release bupropion hydrochloride tablet having 100 mg of bupropion hydrochloride was formed by weighing each component and providing each component except for the lubricant and glidant to a V-blender and mixed for 5–15 min at low shear conditions. The lubricant, magnesium stearate, and the glidant, colloidal silicon dioxide, were then added to the formulation and blended at the same rate for an additional 3–7 min. The formulation was as set forth in Table 1.

TABLE 1

| Component | Weight (mg) |
| --- | --- |
| Bupropion hydrochloride | 100.00 |
| Lactose, anhydrous | 136.32 |
| Polyethylene oxide | 42.00 |
| Colloidal silicon dioxide | 0.28 |
| Magnesium Stearate | 1.40 |
| Total | 280.00 |

The formulation of Table 1 was directly compressed using a Manesty, rotary-type tablet press into tablets. The tablets were monitored for weight, hardness, thickness and friability. The hardness was adjusted to between 5 and 12 kp, preferably between 7 and 9 kp. The tablet thickness ranged from 0.170 in to about 0.195 in. Friability was maintained below 1%.

EXAMPLE 2

A direct compression formulation of bupropion hydrochloride extended-release formulation including a dosage of 150 mg of bupropion was prepared using the blending conditions and procedure of Example 1. The components combined are set forth in the amounts weighed out initially in Table 2.

TABLE 2

| Component | Weight (mg) |
| --- | --- |
| Bupropion hydrochloride | 150.00 |
| Lactose, anhydrous | 204.48 |
| Polyethylene oxide | 63.00 |
| Colloidal silicon dioxide | 0.42 |
| Magnesium Stearate | 2.10 |
| Total | 420.00 |

The formulation in Table 2 was directly compressed and monitored for weight, hardness, thickness and friability using the same apparatus and procedure as Example 1, but using larger tablet tooling.

EXAMPLE 3

A direct compression formulation bupropion hydrochloride tablet having 100 mg of bupropion hydrochloride was formed which also included potassium metabisulfite as a stabilizer. The formulation was prepared in accordance with the same procedure and under the same conditions as Example 1 with the lubricant and glidant being provided after initially blending the other the other components.

TABLE 3

| Component | Weight (mg) |
|---|---|
| Bupropion hydrochloride | 100.00 |
| Lactose, anhydrous | 135.62 |
| Polyethylene oxide | 42.00 |
| Potassium metabisulfite | 0.70 |
| Colloidal silicon dioxide | 0.28 |
| Magnesium Stearate | 1.40 |
| Total | 280.00 |

After combining the components in the formulation of Table 3, the formulation was directly compressed using the apparatus described in Example 1.

EXAMPLE 4

A direct compression formulation bupropion hydrochloride tablet having 100 mg of bupropion hydrochloride was formed which also included sodium bisulfite as a stabilizer. The formulation was prepared in accordance with the same procedure and under the same conditions as Example 1, and the magnesium stearate and colloidal silicon dioxide were added after initially blending the other components.

TABLE 4

| Component | Weight (mg) |
|---|---|
| Bupropion hydrochloride | 100.00 |
| Lactose, anhydrous | 135.62 |
| Polyethylene oxide | 42.00 |
| Sodium bisulfite | 0.70 |
| Colloidal silicon dioxide | 0.28 |
| Magnesium Stearate | 1.40 |
| Total | 280 |

After combining the components in the formulation of Table 4, the formulation was directly compressed using the apparatus described in Example 1.

EXAMPLE 5

A direct compression formulation bupropion hydrochloride tablet having 100 mg of bupropion hydrochloride was formed using hydroxypropyl cellulose in place of polyethylene oxide as a binder. The formulation was prepared in accordance with the same procedure and under the same conditions as Example 1.

TABLE 5

| Component | Weight (mg) |
|---|---|
| Bupropion hydrochloride | 100.00 |
| Lactose, anhydrous | 136.32 |
| Hydroxypropyl Cellulose | 42.00 |
| Colloidal silicon dioxide | 0.28 |
| Magnesium Stearate | 1.40 |
| Total | 280.00 |

After combining the components in the formulation of Table 5, the formulation was directly compressed using the apparatus described in Example 1.

EXAMPLE 6

A direct compression formulation bupropion hydrochloride tablet having 100 mg of bupropion hydrochloride was formed using hydroxypropyl cellulose as the binder in the same manner as Example 5. However, the formulation also included potassium metabisulfite as a stabilizer. The formulation was prepared using the procedure and shear mixing conditions described in Example 3.

TABLE 6

| Component | Weight (mg) |
|---|---|
| Bupropion hydrochloride | 100.00 |
| Lactose, anhydrous | 135.62 |
| Hydroxypropyl Cellulose | 42.00 |
| Potassium metabisulfite | 0.70 |
| Colloidal silicon dioxide | 0.28 |
| Magnesium Stearate | 1.40 |
| Total | 280.00 |

After combining the components in the formulation of Table 6, the formulation was directly compressed using the apparatus described in Example 1.

EXAMPLE 7

A direct compression formulation bupropion hydrochloride tablet having 100 mg of bupropion hydrochloride was formed using hydroxypropyl cellulose as the binder in the same manner as Example 5. However, the formulation also included sodium bisulfite as a stabilizer. The formulation was prepared using the procedure and shear mixing conditions described in Example 4.

TABLE 7

| Component | Weight (mg) |
|---|---|
| Bupropion hydrochloride | 100.00 |
| Lactose, anhydrous | 135.62 |
| Hydroxypropyl Cellulose | 42.00 |
| Sodium bisulfite | 0.70 |
| Colloidal silicon dioxide | 0.28 |
| Magnesium Stearate | 1.40 |
| Total | 280.00 |

After combining the components in the formulation of Table 7, the formulation was directly compressed using the apparatus described in Example 1.

EXAMPLE 8

A direct compression formulation bupropion hydrochloride tablet having 150 mg of bupropion hydrochloride was formed using polyethylene oxide as the binder in the same manner as Example 2. However, the formulation also included potassium metabisulfite as a stabilizer. The formulation was prepared using the procedure and shear mixing conditions described in Example 3.

TABLE 8

| Component | Weight (mg) |
|---|---|
| Bupropion hydrochloride | 150.00 |
| Lactose, anhydrous | 203.43 |
| Polyethylene oxide | 63.00 |
| Potassium metabisulfite | 1.05 |

TABLE 8-continued

| Component | Weight (mg) |
| --- | --- |
| Colloidal silicon dioxide | 0.42 |
| Magnesium Stearate | 2.10 |
| Total | 420.00 |

The formulation in Table 8 was directly compressed using the same apparatus as Example 2.

EXAMPLE 9

A direct compression formulation bupropion hydrochloride tablet having 150 mg of bupropion hydrochloride was formed using polyethylene oxide as the binder in the same manner as Example 2. However, the formulation also included potassium metabisulfite as a stabilizer. The formulation was prepared using the procedure and shear mixing conditions described in Example 4.

TABLE 9

| Component | Weight (mg) |
| --- | --- |
| Bupropion hydrochloride | 150.00 |
| Lactose, anhydrous | 203.43 |
| Polyethylene oxide | 63.00 |
| Sodium bisulfite | 1.05 |
| Colloidal silicon dioxide | 0.42 |
| Magnesium Stearate | 2.10 |
| Total | 420.00 |

The formulation in Table 9 was directly compressed using the same apparatus as Example 2 into tablets.

EXAMPLE 10

A direct compression formulation bupropion hydrochloride tablet having 150 mg of bupropion hydrochloride was formed using hydroxypropyl cellulose as the binder in the same manner as Example 2. The formulation was prepared using the procedure and shear mixing conditions described in Example 2.

TABLE 10

| Component | Weight (mg) |
| --- | --- |
| Bupropion hydrochloride | 150.00 |
| Lactose, anhydrous | 204.48 |
| Hydroxypropyl Cellulose | 63.00 |
| Colloidal silicon dioxide | 0.42 |
| Magnesium Stearate | 2.10 |
| Total | 420.00 |

The formulation in Table 10 was directly compressed using the same apparatus as Example 2 into tablets.

EXAMPLE 11

A direct compression formulation bupropion hydrochloride tablet having 150 mg of bupropion hydrochloride was formed using hydroxypropyl cellulose as the binder in the same manner as Example 2. However, the formulation also included potassium metabisulfite as a stabilizer. The formulation was prepared using the procedure and shear mixing conditions described in Example 3.

TABLE 11

| Component | Weight (mg) |
| --- | --- |
| Bupropion hydrochloride | 150.00 |
| Lactose, anhydrous | 203.43 |
| Hydroxypropyl Cellulose | 63.00 |
| Potassium metabisulfite | 1.05 |
| Colloidal silicon dioxide | 0.42 |
| Magnesium Stearate | 2.10 |
| Total | 420.00 |

The formulation in Table 11 was directly compressed using the same apparatus as Example 2 into tablets.

EXAMPLE 12

A direct compression formulation bupropion hydrochloride tablet having 150 mg of bupropion hydrochloride was formed using hydroxypropyl cellulose as the binder in the same manner as Example 2. However, the formulation also included sodium bisulfite as a stabilizer. The formulation was prepared using the procedure and shear mixing conditions described in Example 4.

TABLE 12

| Component | Weight (mg) |
| --- | --- |
| Bupropion hydrochloride | 150.00 |
| Lactose, anhydrous | 203.43 |
| Hydroxypropyl Cellulose | 63.00 |
| Sodium bisulfite | 1.05 |
| Colloidal silicon dioxide | 0.42 |
| Magnesium Stearate | 2.10 |
| Total | 420.00 |

The formulation in Table 12 was directly compressed using the same apparatus as Example 2 into tablets.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method for tableting bupropion hydrochloride by direct compression without employing a slugging or wet granulation step comprising the steps of:
    (a) weighing bupropion hydrochloride and exicipients, said bupropion hydrochloride having a particle size of from about 130 to about 450 microns and a density of from about 0.44 to about 0.66 g/ml;
    (b) combining the bupropion hydrochloride and the excipients to form a directly compressible formulation; and
    (c) directly compressing the formulation to form bupropion hydrochloride tablets.

2. The method according to claim 1, wherein step (b) further comprises blending the bupropion hydrochloride and excipients under low shear conditions.

3. The method according to claim 1, wherein the formulation is directly compressed in a compression die.

4. The method according to claim 3, wherein the formulation is directly compressed using a rotary tablet machine.

5. The method according to claim 1, wherein step (c) further comprises compressing the tablets to a hardness of from about 5 to about 12 kp and a thickness of from about 0.170 in. (0.431 cm) to about 0.195 in. (0.495 cm).

6. The method according to claim 1, wherein the excipients comprise a binder, a filler, a glidant, and a lubricant.

7. The method according to claim 6, wherein the binder is polyethylene oxide.

8. The method according to claims 6, wherein the binder is hydroxypropyl cellulose.

9. The method according to claim 6, wherein the filler is lactose.

10. The method according to claim 1, wherein the excipients are combined by blending at a rate of from about 4 to about 30 rpm.

11. The method according to claim 1, wherein the excipients comprise a lubricant and a glidant and step (b) further comprises combining the bupropion hydrochloride and the excipients other than the lubricant and the glidant prior to adding and combining the lubricant and glidant.

12. The method according to claim 1, further comprising weighing the bupropion hydrochloride and the excipients such that the directly compressible formulation comprises on a solids basis:
   (i) from about 30 to about 40 percent by weight of the bupropion hydrochloride;
   (ii) from about 10 to about 20 percent by weight of a binder;
   (iii) from about 40 to about 60 percent by weight of a filler;
   (iv) from about 0.1 to about 2 percent by weight of a glidant; and
   (v) from about 0.1 to about 2 percent by weight of a lubricant.

13. The method according to claim 12, wherein the binder is polyethylene oxide binder, the filler is lactose, the glidant is colloidal silicon dioxide, and the lubricant is magnesium stearate.

14. The method according to claim 12, wherein the binder is hydroxypropyl cellulose, the filler is lactose, the glidant is colloidal silicon dioxide, and the lubricant is magnesium stearate.

15. The method according to claim 1, wherein the formulation is an extended release formulation ant the bupropion hydrochloride comprises from about 100 mg to about 150 mg of the formulation.

16. The method according to claim 13, wherein the lactose has a density of from about 0.5 to about 1.0 g/ml.

17. The method according to claim 13, wherein the polyethylene oxide has a particle size in the range of from about 840 to about 2,000 microns.

18. The method according to claim 17, wherein the polyethylene oxide has a density range of from about 1.15 to about 1.26 g/ml, a molecular weight of from about 300,000 to about 5,000,000 and a viscosity of from about 8,800 to about 17,600 cp.

19. The method according to claim 18, wherein the polyethylene oxide has a molecular weight of about 5,000,000.

20. The method according to claim 14, wherein the hydroxypropyl cellulose has a particle sized of from about 175 to about 600 microns, a density of from about 0.3 to about 0.7 g/ml, a viscosity of from about 300 to about 3,000 centipoise and a molecular weight of from about 70,000 to about 1,150,000.

21. The method according to claim 1, wherein the formulation further comprises a stabilizer.

22. The method according to claim 21, wherein the stabilizer is selected from the group consisting of organic acid, carboxylic acids, acid salts of amino acids and sulfites.

23. The method according to claim 22, wherein the sulfites comprise potassium metabisulfite and sodium bisulfite.

* * * * *